US010105228B2

(12) United States Patent
Perito

(10) Patent No.: US 10,105,228 B2
(45) Date of Patent: Oct. 23, 2018

(54) SYSTEM AND METHOD FOR NONSURGICAL PENILE GIRTH ENHANCEMENT

(71) Applicant: Paul E. Perito, Coral Gables, FL (US)

(72) Inventor: Paul E. Perito, Coral Gables, FL (US)

( * ) Notice: Subject to any disclaimer, the term of this patent is extended or adjusted under 35 U.S.C. 154(b) by 0 days.

(21) Appl. No.: 15/348,324

(22) Filed: Nov. 10, 2016

(65) Prior Publication Data
US 2017/0128213 A1    May 11, 2017

Related U.S. Application Data

(60) Provisional application No. 62/253,331, filed on Nov. 10, 2015.

(51) Int. Cl.
| A61F 2/26 | (2006.01) |
| A61B 17/34 | (2006.01) |
| A61L 27/20 | (2006.01) |
| A61L 27/54 | (2006.01) |
| A61M 5/32 | (2006.01) |
| A61B 17/00 | (2006.01) |

(52) U.S. Cl.
CPC ............ *A61F 2/26* (2013.01); *A61B 17/3468* (2013.01); *A61L 27/20* (2013.01); *A61L 27/54* (2013.01); *A61M 5/32* (2013.01); *A61B 2017/00792* (2013.01); *A61L 2300/402* (2013.01); *A61L 2400/06* (2013.01); *A61M 5/3204* (2013.01); *A61M 2210/167* (2013.01)

(58) Field of Classification Search
CPC .................................. A61L 27/20; A61F 2/26
USPC ...................................... 600/38–41; 128/898
See application file for complete search history.

(56) References Cited

U.S. PATENT DOCUMENTS

| 6,418,934 | B1 * | 7/2002 | Chin | ......................... A61F 2/26 |
| | | | | 128/898 |
| 8,450,475 | B2 | 5/2013 | Lebreton | |
| 8,357,795 | B2 | 7/2013 | Lebreton | |
| 8,703,118 | B2 * | 4/2014 | Schroeder | ............... A61L 27/26 |
| | | | | 424/78.3 |

(Continued)

FOREIGN PATENT DOCUMENTS

| CN | 102350276 B | 3/2013 |
| CN | 104086788 B | 8/2016 |
| EP | 0784987 B1 | 10/2003 |

OTHER PUBLICATIONS

International Search Report and Written Opinion dated Jan. 24, 2017 for PCT/US16/61286 filed Nov. 10, 2016.

(Continued)

*Primary Examiner* — Samuel Gilbert
(74) *Attorney, Agent, or Firm* — Fleit Gibbons Gutman Bongini & Bianco PL; Paul D. Bianco

(57) ABSTRACT

A system and method for nonsurgical penile girth enhancement. Hydro-dissection creates a space along a length of the penis between Buck's Fascia and Darte's fascia. The filler material, such as hyaluronic acid, is injected into the space created and is modeled after injection. During the same procedure or a later procedure, additional spaces can be created and injected with the filler material, until the desired girth is obtained. The amount of filler material injected during any given procedure is limited to avoid challenging the lymphatics of the penis. By staging the girth enhancing injections, the risk of penile granulomas can be minimized, if not eliminated.

18 Claims, 11 Drawing Sheets

(56) References Cited

U.S. PATENT DOCUMENTS

| | | |
|---|---|---|
| 8,822,676 B2 | 9/2014 | Lebreton |
| 9,089,518 B2 | 7/2015 | Lebreton |
| 9,089,519 B2 | 7/2015 | Lebreton |
| 9,493,755 B2 | 11/2016 | Guo et al. |
| 2006/0096603 A1 | 5/2006 | Choi et al. |
| 2008/0051625 A1 | 2/2008 | Moore |
| 2010/0043807 A1 | 2/2010 | Kim |
| 2010/0174132 A1* | 7/2010 | Gellman .......... A61B 17/00234 600/30 |
| 2013/0041039 A1* | 2/2013 | Lebreton ................ A61K 8/42 514/626 |
| 2016/0354516 A1* | 12/2016 | Chuang ............. A61B 17/3468 |

OTHER PUBLICATIONS

International Preliminary Report on Patentability dated May 15, 2018 for PCT/US16/61286 filed Nov. 10, 2016.

Du Geon Moon, et al., Glans Penis Augmentation Using Hyaluronic Acid Gel as an Injectable Filler, The World Journal of Men's Health, Aug. 2015, 33(2); 50-61.

Tae Il Kwak, MD, et al., The Effects of Penile Girth Enhancement Using Injectable Hyaluronic Acid Gel, a Filler; 2010 Copyright, International Society for Sexual Medicine, 2011; 8: 3407-3413.

\* cited by examiner

SYSTEM AND METHOD FOR NONSURGICAL PENILE GIRTH ENHANCEMENT

FIELD OF THE DISCLOSURE

The disclosure relates to a system and method for nonsurgical penile girth enhancement. The disclosure also relates more generally to a nonsurgical system and method for changing the shape of the penis.

BACKGROUND

FIG. 1 is a cross section of the penis showing the anatomy. In addition to the text labelling the anatomy, the numbers 12, 3, 6, and 9 (like a face of a clock) are reference points for determining the position of the injections as discussed below. FIG. 2 also shows the anatomy of the penis and is a perspective view with various layers dissected away for identification purpose. For both FIG. 1 and FIG. 2, the anatomical features have been assigned the reference numerals as indicated in the Reference Numeral List at the end of this specification.

There can be physiological (e.g. trauma) and/or psychological bases that warrant consideration of penile girth enhancement. Penile dysmorphophobia is defined as a condition in those men whose penis are normal, but request an augmentation procedure as a result of an altered perception of the organ. Penile dysmorphophopia can be both a functional issue as well as an aesthetic issue. Dating back to the ancient Greeks and perhaps even further, men, regardless of age, have considerable concern for penis size, including girth, and other aesthetic features of the penis.

Despite this long-felt need, neither the Society of Sexual Medicine nor the American Urologic Association has sanctioned any treatment related to penile length and/or girth enhancement. To the contrary, the position of the Society of Sexual Medicine is:

The Society for the Study of Impotence has found no peer reviewed, objective or independently monitored studies, or other data, which prove the safety and efficacy of penile lengthening or girth enhancement surgery. Therefore, penile lengthening and girth enhancement surgery can only be regarded as experimental.

With respect to penile girth enhancement, current techniques include: 1. Fat Transfer Surgery; 2. Dermal Fat Grafts; 3. Acellular Dermal Matrix; and 4. "non-conventional" filler materials such as paraffin wax, mineral oil, and silicone.

There are centers that report good results with free fat transfer surgery, but surgeons and patients always need to be concerned about the development of granulomatous changes in the fat occurring after the natural and expected revascularization of the fatty deposits.

Some centers have previously reported on dermal fat grafts taken from the groin or gluteal creases, but the surgeon and the patient need to be concerned about a long post-operative recovery period and the potential for serious complications such as penile shortening, penile curvature, and loss of the graft.

The use of layered (1 to 6 layers; 0.89 to 1.65 mm thickness) acellular dermal matrix circumferentially has also been described claiming rapid revascularization and subsequent tissue regeneration. Unfortunately, with infection rates reported as high as 22%, this novel technology has been essentially discarded.

With respect to the "unconventional" materials, these border on being criminal and are usually utilized by unlicensed practitioners under less than ideal conditions.

Despite these limitations, penile girth enhancement is still very much wanted. As a result, what is needed is a system and method for nonsurgical penile girth enhancement.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

SUMMARY OF THE DISCLOSURE

Figure 1:
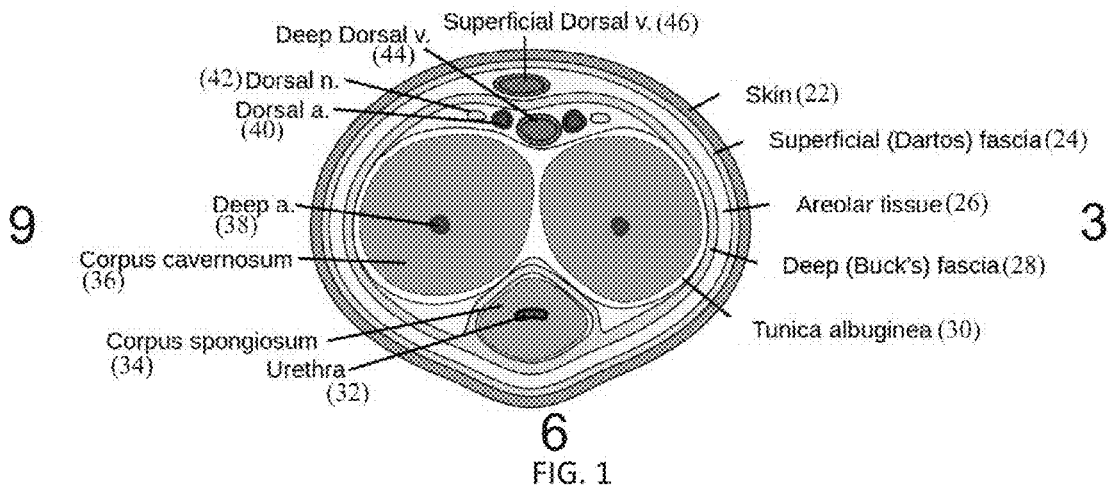
FIG. 1 is a cross section of the penis showing the anatomy. In addition to the text labelling the anatomy, the numbers 12, 3, 6, and 9 (like a face of a clock) are reference points for determining the position of the injections.
Figure 2:
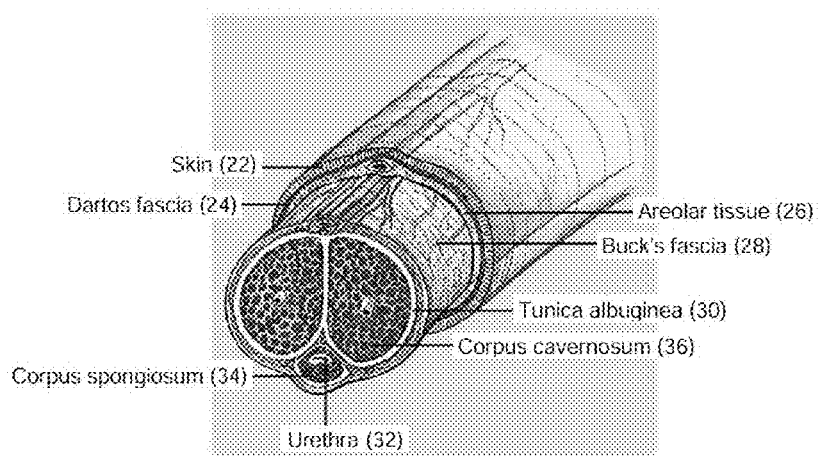
FIG. 2 is a perspective view of the penis with various layers dissected away for identification purpose.

One aspect of the disclosure relates to a method for increasing girth of a penis. A first space is created along a length of the penis between Buck's Fascia of the penis and Darte's fascia of the penis, an injectable filler material is injected into the first space; and the filler material is modeled in the first space.

In an exemplary embodiment, the filler material includes hyaluronic acid. The hyaluronic acid can be a cross-linked hyaluronic acid. The filler material can be a gel.

The method can further comprise creating a second space along a length of the penis between Buck's Fascia of the penis and Darte's fascia of the penis; injecting the injectable filler material into the second space; and modeling the filler material in the second space. The second space is created at a different location than the first space.

In some embodiments creating, injecting, and modeling of the first space and creating, injecting, and modeling of the second space occur during a first procedure. The method can further comprise creating a third space along a length of the penis between Buck's Fascia of the penis and Darte's fascia of the penis; injecting the injectable filler material into the third space; and modeling the filler material in the third space. The third space is created at a different location than the first and second spaces. The creating, injecting, and modeling of the third space occur during a second procedure, with the second procedure occurring after the first procedure. In an exemplary embodiment, the second procedure occurs at least two weeks after the first procedure.

In some embodiments, the first space is created on a first lateral side of the penis and the second space is created on a second lateral side of the penis.

Creating the first, second, and third spaces can include hydro-dissection. The hydro-dissection can include injecting a fluid with a needle. The fluid can include an anesthetizing agent.

In one embodiment, approximately 3 ml of the fluid is injected to create the first space, approximately 3 ml of the fluid is injected to create the second space, and approximately 3 ml of the fluid is injected to create the third space. In another exemplary aspect, approximately 1 ml of the filler material is injected in the first space, approximately 1 ml of the filler material is injected in the second space, and approximately 1 ml of the filler material is injected in the third space.

Another aspect of the disclosure relates to a system for increasing girth of a penis. The system comprises: an injectable fluid for hydro-dissection to create a space between Buck's Fascia and Dartos Fascia along a length of the penis; and an injectable filler material for injection into the created space. The injectable filler material includes hyaluronic acid and a first volume of injectable filler material is injected during a first procedure and a second volume of injectable filler material is injected during a second procedure. The second procedure occurs at least two weeks after the first procedure.

Another aspect of the disclosure relates to the use of hyaluronic acid as an injectable filler material to increase girth of a penis. The filler material is injected into a first space created along a length of the penis between Buck's Fascia of the penis and Darte's fascia of the penis. The filler material is modeled after injection into the first space.

The use can further include injecting the filler material into a second space created along a length of the penis between Buck's Fascia of the penis and Darte's fascia of the penis, with the second space created at a location different than a location of the first space. In one embodiment, both the first and second spaces are created and injected with the filler material during an initial treatment.

The use can further include injecting the filler material into a third space created along a length of the penis between Buck's Fascia of the penis and Darte's fascia of the penis, with the third space created at a location different than the first and second spaces. The third space is created and injected with the filler material during a subsequent treatment. The subsequent treatment can occur at least two weeks after the initial treatment.

In an exemplary embodiment, the first space is created on a first lateral side of the penis and the second space is created on a second lateral side of the penis.

In some uses, the hyaluronic acid is a cross-linked hyaluronic acid.

In some exemplary uses, at least one of the first space, second space, and third space is created by hydro-dissection. The hydro-dissection can include injecting a fluid, which can include an anesthetizing agent, with a needle. Although the volume of fluid can vary, an exemplary embodiment involves approximately 3 ml of the fluid injected to create the first space, approximately 3 ml of the fluid injected to create the second space, and approximately 3 ml of the fluid injected to create the third space. The volume of filler material can also vary, but an exemplary embodiment involves approximately 1 ml of the filler material injected in the first space, approximately 1 ml of the filler material injected in the second space, and approximately 1 ml of the filler material injected in the third space.

DETAILED DESCRIPTION

As required, embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

One aspect of the disclosure relates to a filler material that includes hyaluronic acid (HA), which can be a cross-linked hyaluronic acid. The ideal filler material should be biocompatible, non-antigenic, non-pyrogenic, non-inflammatory, non-toxic, easy to use, stable after injection, non-migratory, long-lasting but resorbable, natural looking, and not too expensive. A ubiquitous component of all mammalian connective tissue, HA, is a naturally occurring polysaccharide, with the same chemical and molecular composition in all species; and occurring in the intercellular matrix of dermal layers of the skin of all species. Therefore, HA sourced from animals can be used in humans, making it highly biocompatible without creating foreign body reactions. The HA matrix has an enormous ability to bind water (water content greater than 99%) and form hydrated polymers of high viscosity. HA resides in the extracellular space and functions as a space-filling, structure-stabilizing, and cell-protective molecule with uniquely malleable physical properties and superb biocompatibility. Restylane, Perlane (Q-Med, Uppsala, Sweden) and Juvederm (Allergan, Calif.) are injectable HA gels contemplated by the disclosure. The composition disclosed in U.S. Pat. Nos. 8,357,795; 8,450,475; 8,822,676; 9,089,518; and 9,089,519 are other exemplary embodiments contemplated by this disclosure. HA is a glycosaminoglycan biopolymer composed of alternating residues of the monosaccharides D-glucuronic acid and N-acetyl-D glucosamine linked in repeating units. The molecular weight of HA in its pure form can be determined. However, HA in its pure form is not stabilized. Injectable HA gel is an HA product chemically modified to increase its longevity in the tissue and to form a gel.

HA aggregates imbibe water and are responsible for resilience to compression. This tendency to hydrophilic action leads to its bioelasticity, rendering the penis with a natural feel both in the flaccid and tumescent state. HA also contributes to tissue hydrodynamics and thus movement and proliferation of cells, further lending to its innate anti-inflammatory effect. HA also promotes tissue ingrowth.

The disclosure also relates to a procedure for penile injection with a filler material (HA or some other suitable filler). In one embodiment, the procedure relates to the proper plane for depositing the material, thus limiting the reabsorption secondary to hyaluronidases. After prepping and draping the groin in the usual sterile fashion, hydro-dissection is used to create a plane (i.e. a space or envelope) between Buck's Fascia, which surrounds the corpora creating a natural barrier, and the extension of Darte's Fascia down the length of the penis. This region (areolar tissue) contains very few vessels and offers a benign region for girth enhancement. Hydro-dissection is accomplished by injection of saline (3 ml for example) or 1% lidocaine or some other anesthetizing agent along the length of the phallus within the aforementioned plane, using a suitably sized needle, a non-limiting example of which is a 22 gauge 1½ inch needle.

Several injections can be given, preferably at different time points. In one particularly effective approach, during an initial treatment, two injections are given laterally at 3 and 9 o'clock (viewing the circumference of the penis as a clock). During one or more subsequent treatments, injections are given at one or more of the following orientations—10, 2, 12, 4 and 8 o'clock, depending upon the patient's desired girth endpoint. Each hydro-dissected channel is filled with the filler material (for hydro-dissection with 3 ml of fluid, 1 ml of HA has been found effective, but other amounts and different fillers are contemplated by the disclosure). Any suitable injection apparatus can be used, a non-limited example of which is a 22 gauge 1½ inch needle. The injected HA "cylinder" is then molded or otherwise shaped by the practitioner. This molding or shaping can even be done by hand, without the need for any tools, if desired.

If more than one injection is given during a procedure, the disclosure contemplates that all the spaces can be created first, then all the spaces are injected with the filler material, and then the molding or shaping occurs. Alternatively, the first space is created, injected, and molded and then the second space is created, injected, and molded, and so on. Additionally, a final molding or shaping can occur after all the spaces are created, injected, and molded. The disclosure also contemplates that a combination of these approaches could be used.

By staging the girth enhancing injections the risk of penile granulomas, one of the dreaded complications of penile girth enhancement, can be minimized, if not eliminated. When overloaded or violated, the lymphatics of the penis normal inflammatory responses may be altered leading to granulomatous changes and subsequent loss of tissue integrity and a poor, often painful cosmetic results. The patient undergoes 2 to 4 ml of HA injection about every two weeks (at a minimum), never challenging the lymphatics of the penis, until the patient is satisfied with the cosmetic result. Different time periods (i.e. other than two weeks) between injections can be used, if desired.

In experimental studies, a total of 121 patients have been treated for penile girth enhancement. Important parameters to consider when evaluating these results include the mean number of volume of filler material administered per patient, which was 10.7 ml. The mean follow-up was 21.1 months. There were NO complications, a finding similar to HA injections for naso-labial folds. Most important to the findings were the telephone interviews regarding patient satisfaction and patient perception of filler retention. It should be noted that 12.5% of the patients could not be contacted for these endpoints.

Figure 3:
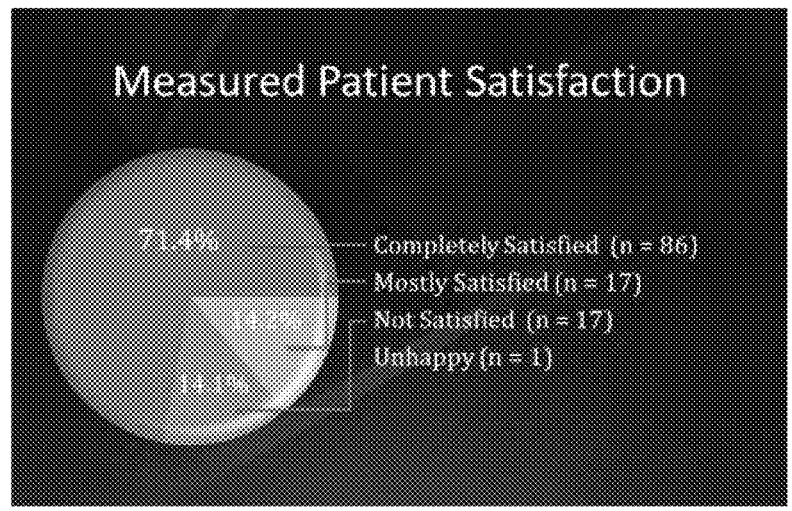
FIG. 3 is a pie graph showing patient satisfaction for experimental results.

As shown in FIG. 3, over 85% of the patients were completely or mostly satisfied with over 70% completely satisfied. Those that were not satisfied tended to be the patients with fewer than five injections, suggesting that the patients may have not been satisfied because they could not complete their course of injections. Only one patient was unhappy because the patient claimed that all of the two ml of filler material injected were re-absorbed.

Figure 4:
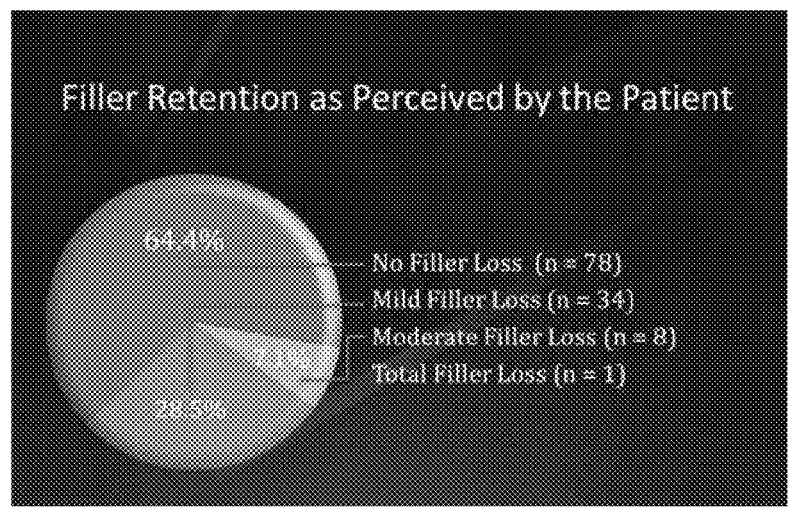
FIG. 4 is a pie graph showing patient perception of filler retention for the experimental results.

As shown in FIG. 4, over 92% of the patients reported no filler loss or only mild filler loss. Moderate filler loss was reported by only 7% of the patients and the same patient that was unhappy reported total filler loss.

Figure 5A:
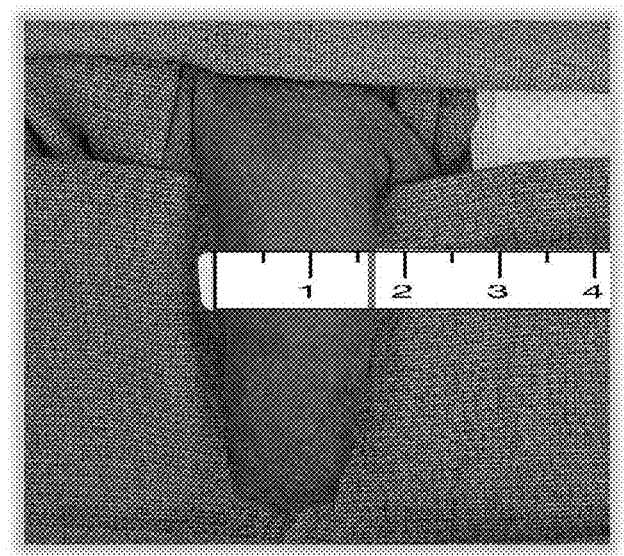
FIG. 5A shows before and FIG. 5B shows after photographs for one patient in the experimental study.
Figure 5B:
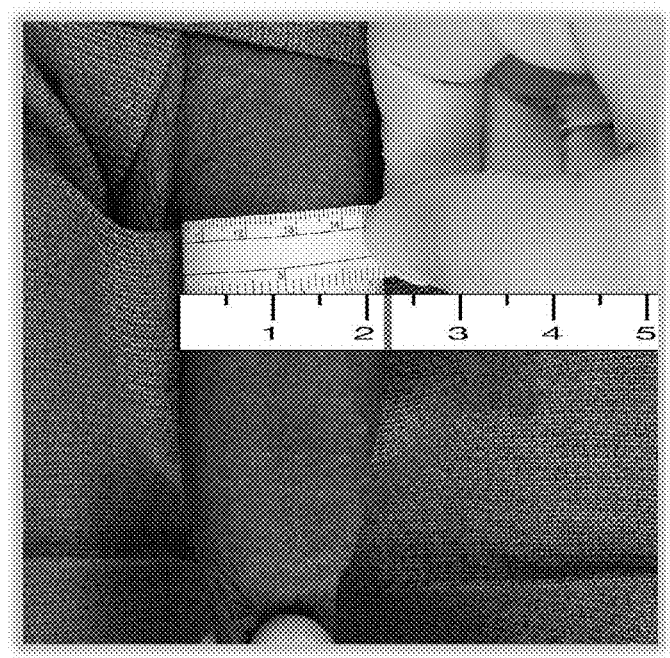

FIG. 5A shows before and FIG. 5B shows after photographs for one patient in the experimental study. In this case, injections were only given at the 3 and 9 clock positions. The increase in diameter is from about 1.6 inches (4.064 cm) to about 2.2 inches (5.588 cm), which calculates as an increase in girth (girth=circumference=$2\pi$radius) from about 5 inches (12.7 cm) to about 6.9 inches (17.526 cm). The increase in girth was confirmed with measurement with a tape measure.

Figure 6A:
FIG. 6A shows before and FIG. 6B shows after photographs for another patient in the experimental study.
Figure 6B:

FIG. 6A shows before and FIG. 6B shows after photographs for one patient in the experimental study. In this case, the patient had a penile implant and was not satisfied with the natural folds that occur in some penile implants when in the flaccid position as shown in FIG. 6A. These natural folds are minimized with properly placed injections with HA filler material as shown in FIG. 6B.

Figure 7A:
FIG. 7A shows before and FIG. 7B shows after photographs for another patient in the experimental study.
Figure 7B:
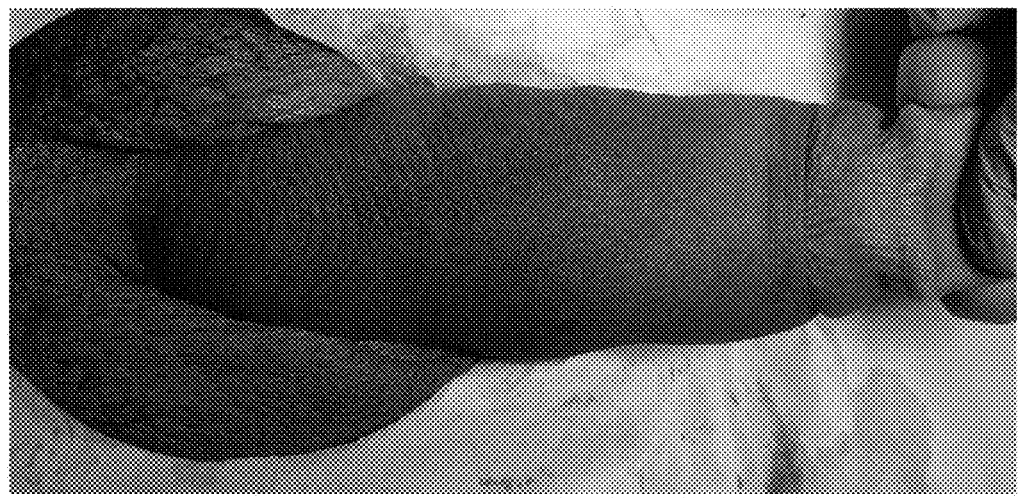

FIG. 7A shows before and FIG. 7B shows after photographs for one patient in the experimental study. In this case, the patient reported occasional preputial edema, especially after intercourse as shown in FIG. 7A. With very selective placement of the HA filler material, the penis has a more natural look, precluding filling of the prepuce with edematous fluid after intercourse as shown in FIG. 7B.

Figure 8A:
FIG. 8A shows before and FIG. 8B shows after photographs for another patient in the experimental study.
Figure 8B:

FIG. 8A shows before and FIG. 8B shows after photographs for one patient in the experimental study. In this case, the patient received two staged injections of a total of 4 ml of HA filler material. The increase in girth is from about 3.75 inches (9.525 cm) as shown in FIG. 8A to about 4.875 inches (12.3825 cm) as shown in FIG. 8B, an increase of about at least one inch (2.54 cm) in girth.

Figure 9:
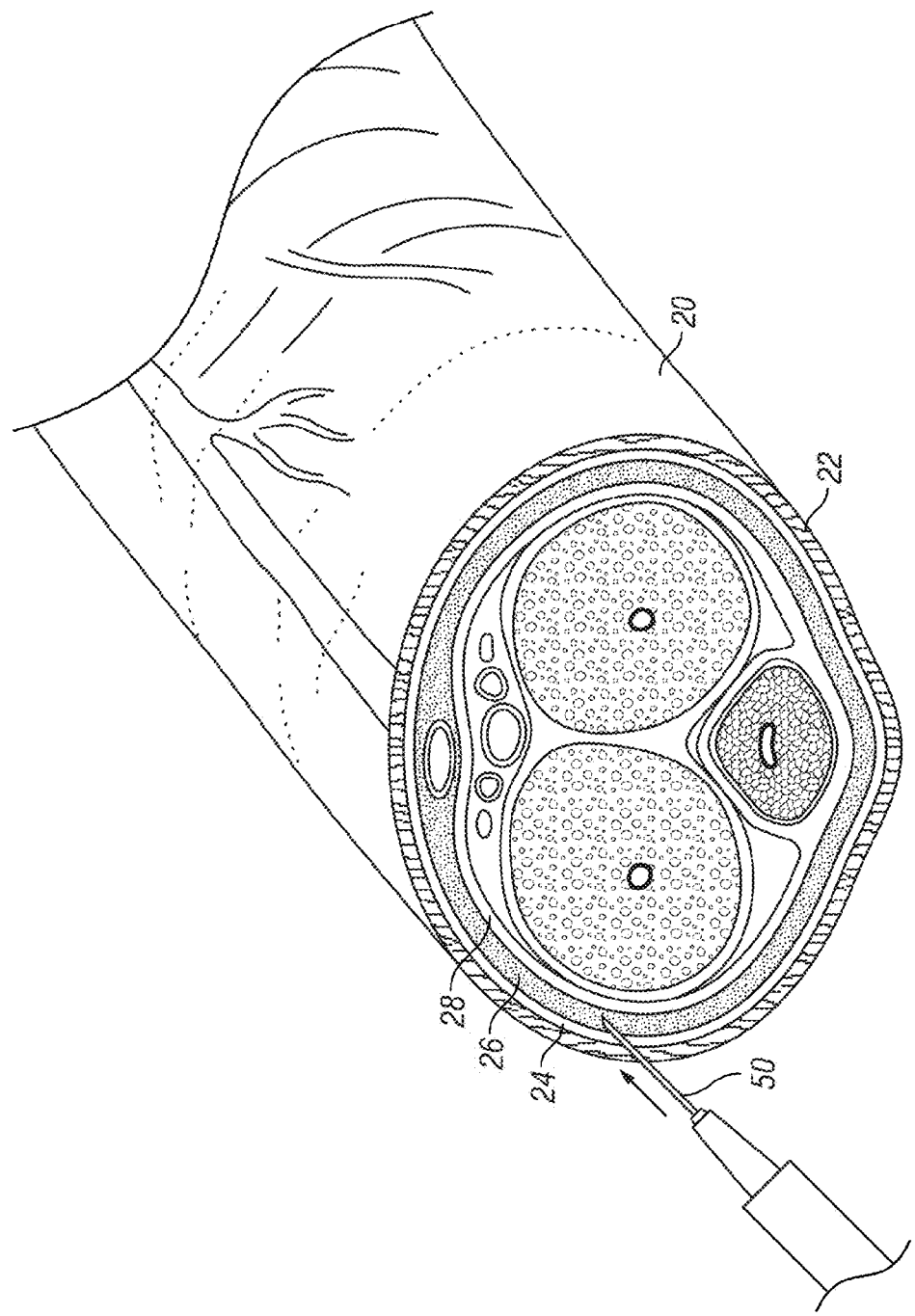
FIG. 9 schematically shows a needle being inserted for hydro-dissection to create a space for the filler material.

The system, method, and use will now be described with reference to FIGS. 9-13. As shown in FIG. 9, a needle 50 penetrates skin 22 and enters areolar tissue 26. Needle 50 is used for hydro-dissection to create a plane (i.e. a space or envelope) between Buck's Fascia 28 and Darte's Fascia 24 along a length of penis 20. Hydro-dissection is accomplished by injection of a fluid such as saline or 1% lidocaine or some other anesthetizing agent along the length of penis 20 within areolar tissue 26, using a suitably sized needle.

Figure 10:
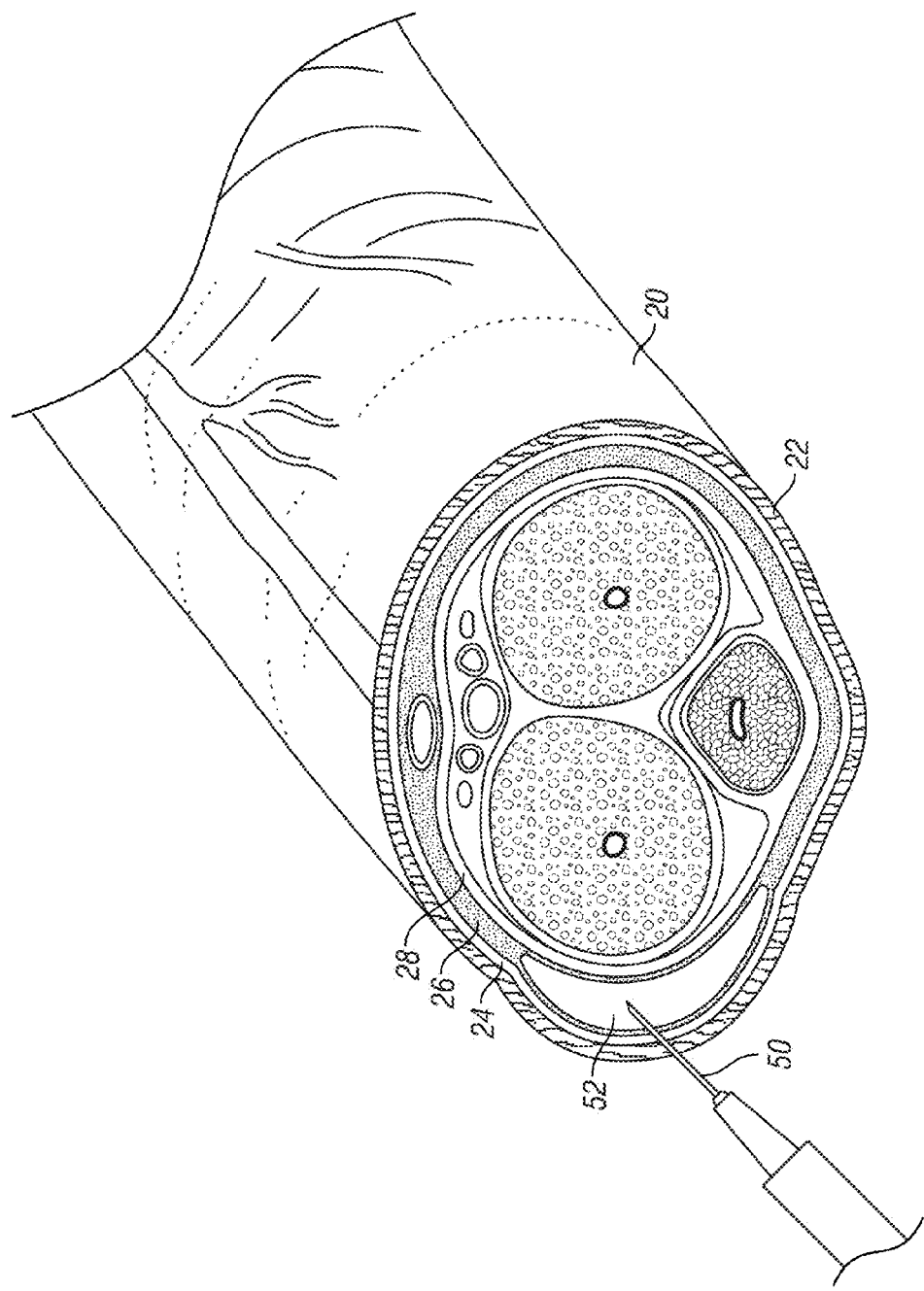
FIG. 10 schematically shows the space created by the hydro-dissection.
Figure 13:
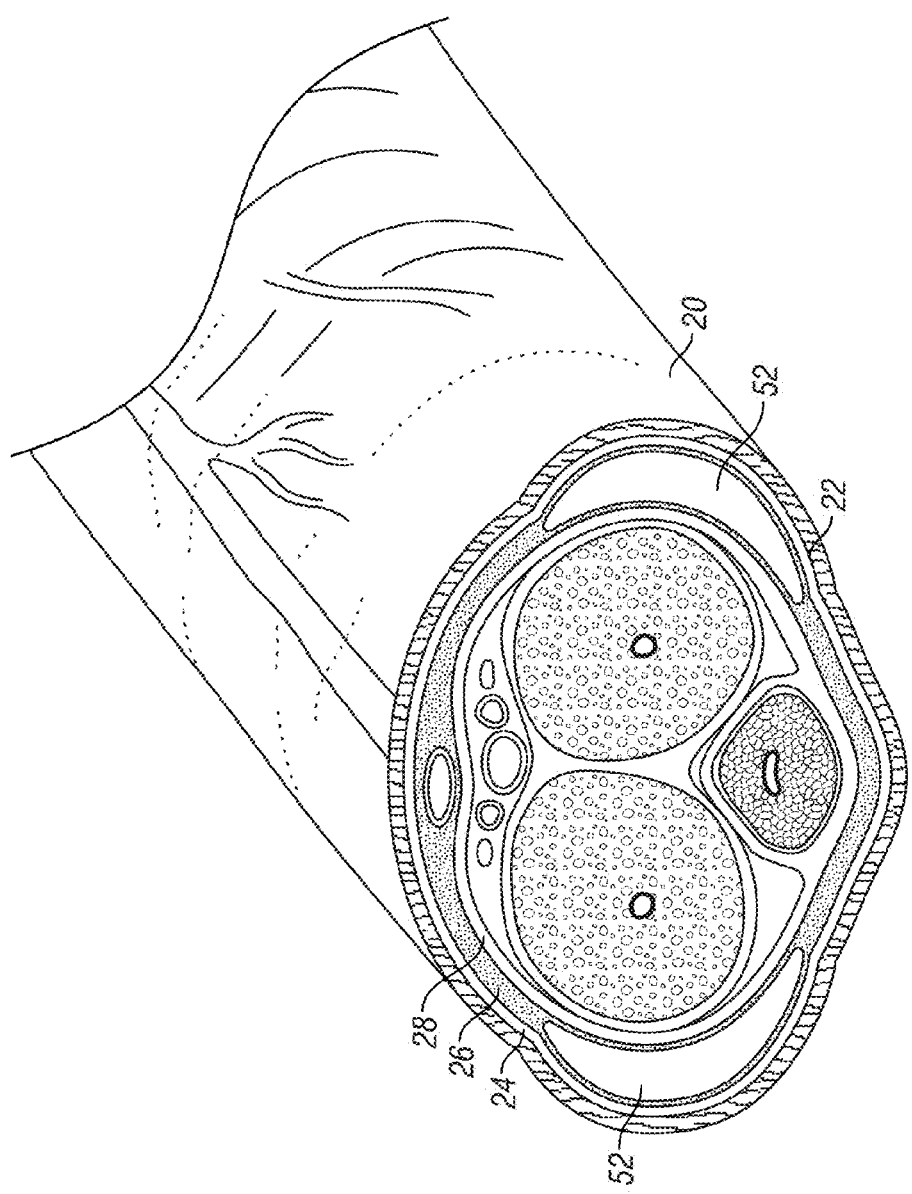
FIG. 13 schematically shows a first space created by hydro-dissection and a second space created by hydro-dissection.

FIG. 10 shows the created space 52 produced by the hydro-dissection. Needle 50 is shown on one lateral side (the 9 o'clock position) of penis 20. In one particularly effective approach, during an initial treatment, two injections (one on each lateral side) are given laterally at 3 and 9 o'clock. During one or more subsequent treatments, injections are given at one or more of the following orientations—10, 2, 12, 4 and 8 o'clock, depending upon the patient's desired girth endpoint. With injections on each lateral side, needle 50 enters skin 22 at different locations (3 and 9 o'clock), and as a result the space created at the 3 o'clock position is created at a different location that the space created at the 9 o'clock position. That said, the disclosure contemplates that the space created by each injection can overlap each other or can be discrete pockets with no overlap. FIG. 13 shows two such discrete pockets with no overlap, with a first space 52 created on a first lateral aspect of penis 20 and a second space 52 created on a second lateral aspect of penis 20.

Figure 11:
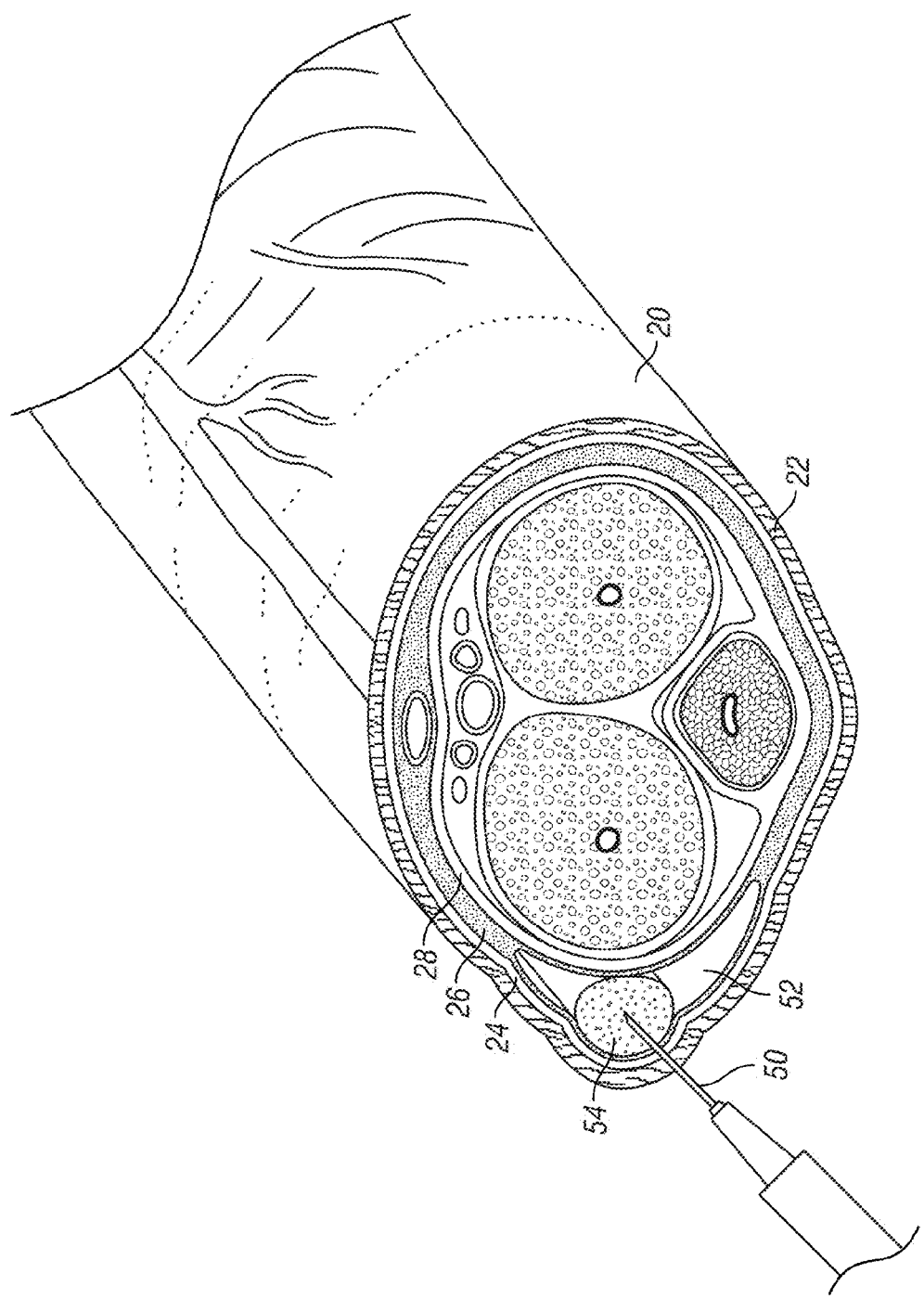
FIG. 11 schematically shows the filler material being injected into the created space.

As shown in FIG. 11, filler material 54 is injected into space 52 by needle 50. The disclosure contemplates that the same needle used for hydro-dissection can be used to inject the filler material or a different needle can be used. For hydro-dissection with 3 ml of fluid, 1 ml of HA has been found effective, but other amounts and different fillers are contemplated by the disclosure.

Figure 12:
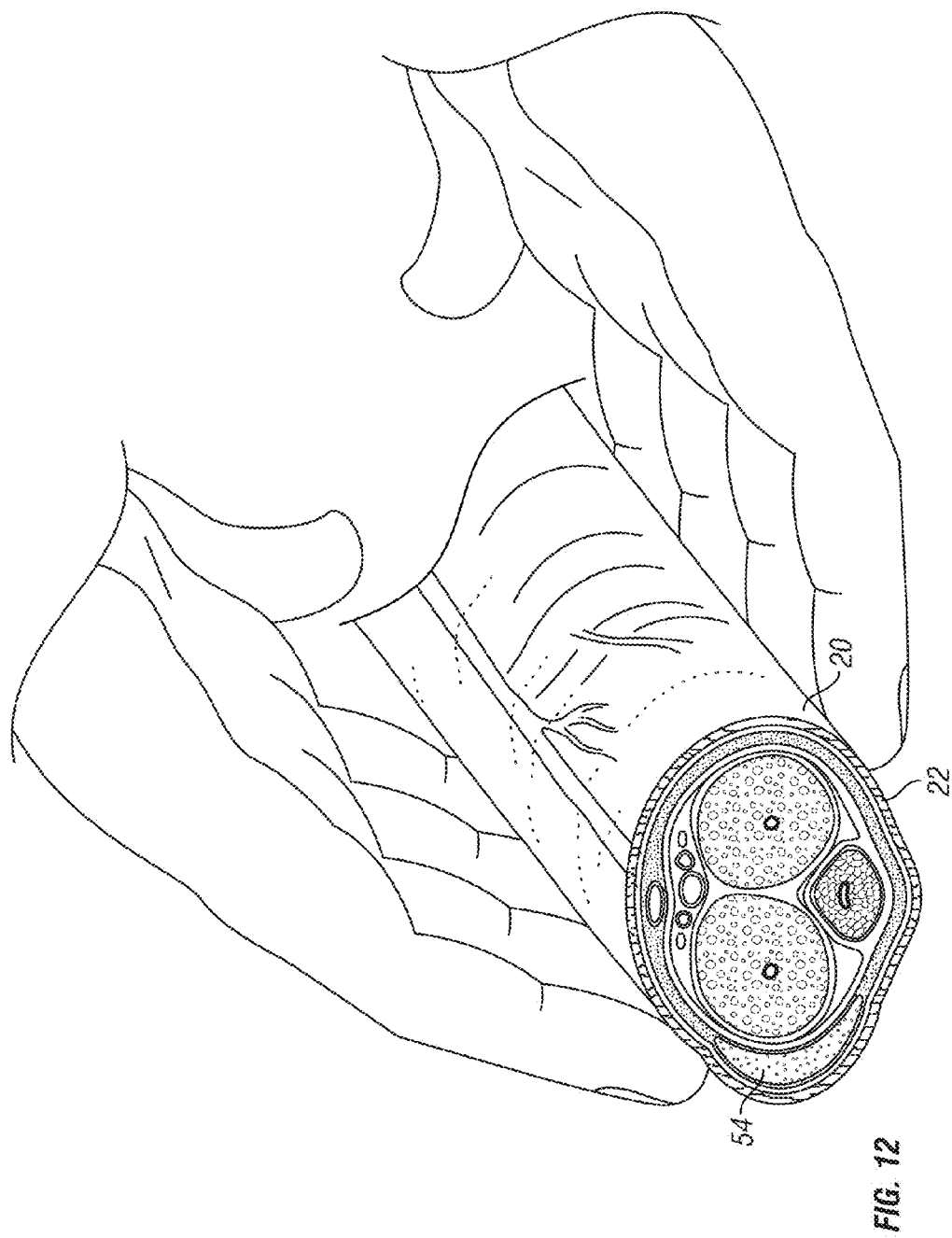
FIG. 12 schematically shows modelling of the injected filler material.

The injected filler material 54 is then modelled, molded, or otherwise shaped by the practitioner as shown in FIG. 12. This shaping can be done by hand, without the need for any tools or with a shaping tool, if desired.

By staging the girth enhancing injections the risk of penile granulomas, one of the dreaded complications of penile girth enhancement, can be minimized, if not eliminated. When overloaded or violated, the lymphatics of the penis normal inflammatory responses may be altered leading to granulomatous changes and subsequent loss of tissue integrity and a poor, often painful cosmetic results. The patient undergoes 2 to 4 ml of HA injection about every two weeks (at a minimum), never challenging the lymphatics of the penis, until the patient is satisfied with the cosmetic result. Different time periods (i.e. other than two weeks) between injections can be used, if desired.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

REFERENCE NUMERAL LIST

20 Penis
22 Skin
24 Superficial (Dartos) fascia
26 Areolar tissue
28 Deep (Buck's) fascia
30 Tunica albuginea
32 Urethra
34 Corpus spongiosum
36 Corpus cavernosum
38 Deep artery
40 Dorsal artery
42 Dorsal nerve
44 Deep dorsal vein
46 Superficial dorsal vein
50 Needle
52 Space
54 Filler material

What is claimed is:

1. A method for increasing girth of a penis, the method comprising:
   creating a first space along a length of the penis between Buck's Fascia of the penis and Darte's fascia of the penis;
   injecting an injectable filler material into the first space; and
   modeling the filler material in the first space,
   wherein creating the first space includes hydro-dissection by injecting a fluid to create the first space between the Buck's Fascia and the Darte's fascia and wherein the fluid is injected prior to injecting the injectable filler material.

2. The method of claim 1, wherein the filler material includes hyaluronic acid.

3. The method of claim 2, wherein the hyaluronic acid is a cross-linked hyaluronic acid.

4. The method of claim 2, wherein the filler material is a gel.

5. The method of claim 4, further comprising:
   creating a second space along the length of the penis between the Buck's Fascia of the penis and the Darte's fascia of the penis;
   injecting the injectable filler material into the second space; and
   modeling the filler material in the second space,
   wherein the second space is created at a different location than the first space.

6. The method of claim 5, wherein creating, injecting, and modeling of the first space and creating, injecting, and modeling of the second space occur during a first procedure.

7. The method of claim 6, further comprising:
   creating a third space along the length of the penis between the Buck's Fascia of the penis and the Darte's fascia of the penis;
   injecting the injectable filler material into the third space; and
   modeling the filler material in the third space,
   wherein the third space is created at a different location than the first and second spaces, wherein creating, injecting, and modeling of the third space occur during a second procedure, and wherein the second procedure occurs after the first procedure.

8. The method of claim 7, wherein the first space is created on a first lateral side of the penis and the second space is created on a second lateral side of the penis.

9. The method of claim 1, wherein the fluid is injected with a needle.

10. The method of claim 9, wherein 3 ml of the fluid is injected to create the first space.

11. The method of claim 10, wherein 1 ml of the filler material is injected in the first space.

12. The method of claim 9, wherein the fluid includes an anesthetizing agent.

13. A method for increasing girth of a penis, the method comprising:
   creating a first space along a length of the penis between Buck's Fascia of the penis and Darte's fascia of the penis;
   injecting an injectable filler material into the first space;
   modeling the filler material in the first space,
   creating a second space along the length of the penis between the Buck's Fascia of the penis and the Darte's fascia of the penis, the second space created at a different location than the first space;
   injecting the injectable filler material into the second space;

modeling the filler material in the second space,
creating a third space along the length of the penis between the Buck's Fascia of the penis and the Darte's fascia of the penis,
injecting the injectable filler material into the third space, and
modeling the filler material in the third space,
wherein creating, injecting, and modeling of the first space and creating, injecting, and modeling of the second space occur during a first procedure,
wherein the third space is created at a different location than the first and second spaces,
wherein creating, injecting, and modeling of the third space occur during a second procedure, and wherein the second procedure occurs after the first procedure,
wherein the first space is created on a first lateral side of the penis and the second space is created on a second lateral side of the penis,
wherein creating the first space includes hydro-dissection by injecting a fluid to create the first space between the Buck's Fascia and the Darte's fascia,
wherein the filler material is a gel that includes hyaluronic acid, and
wherein the second procedure occurs at least two weeks after the first procedure.

14. The method of claim 13, wherein creating the second space includes hydro-dissection by injecting the fluid to create the second space between the Buck's Fascia and the Darte's fascia and creating the third space includes hydro-dissection by injecting the fluid to create the third space between the Buck's Fascia and the Darte's fascia.

15. The method of claim 14, wherein the fluid is injected with a needle.

16. The method of claim 15, wherein 3 ml of the fluid is injected to create the first space, 3 ml of the fluid is injected to create the second space, and 3 ml of the fluid is injected to create the third space.

17. The method of claim 16, wherein 1 ml of the filler material is injected in the first space, 1 ml of the filler material is injected in the second space, and 1 ml of the filler material is injected in the third space.

18. A method for increasing girth of a penis, the method comprising:
creating a first space along a length of the penis between Buck's Fascia of the penis and Darte's fascia of the penis;
injecting an injectable filler material into the first space;
modeling the filler material in the first space, creating a second space along the length of the penis between the Buck's Fascia of the penis and the Darte's fascia of the penis;
injecting the injectable filler material into the second space; and
modeling the filler material in the second space,
wherein the second space is created at a different location than the first space;
wherein creating the first space includes hydro-dissection by injecting a fluid to create the first space between the Buck's Fascia and the Darte's fascia and creating the second space includes hydro-dissection by injecting the fluid to create the second space between the Buck's Fascia and the Darte's fascia; and
wherein the step of creating the first space occurs prior to the step of injecting the injectable filler material into the first space and the step of creating the second space occurs prior to the step of injecting the injectable filler material into the second space.

* * * * *